US010087471B2

(12) United States Patent
Um et al.

(10) Patent No.: US 10,087,471 B2
(45) Date of Patent: Oct. 2, 2018

(54) HYDROLYSATE OF MIXTURE OF SEAWEED BIOMASS AND LIGNOCELLULOSIC BIOMASS TO IMPROVE BIOCHEMICAL AND BIOFUEL PRODUCTION, AND PREPARATION USING THE SAME

(71) Applicant: Korea Institute of Science and Technology, Seoul (KR)

(72) Inventors: Youngsoon Um, Seoul (KR); Yunje Kim, Seoul (KR); Kyung Min Lee, Seoul (KR); Han Min Woo, Seoul (KR); Gyeongtaek Gong, Seoul (KR); Ki Yeon Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 201 days.

(21) Appl. No.: 15/092,829

(22) Filed: Apr. 7, 2016

(65) Prior Publication Data

US 2016/0298146 A1 Oct. 13, 2016

(30) Foreign Application Priority Data

Apr. 9, 2015 (KR) ........................ 10-2015-0050321

(51) Int. Cl.
*C12P 7/02* (2006.01)
*C12P 7/52* (2006.01)
(Continued)

(52) U.S. Cl.
CPC ................. *C12P 7/52* (2013.01); *C12P 19/02* (2013.01); *C12P 19/12* (2013.01);
(Continued)

(58) Field of Classification Search
CPC .. C12P 19/02; C12P 7/00; C12R 1/145; Y02E 50/17
See application file for complete search history.

(56) References Cited

U.S. PATENT DOCUMENTS

2010/0093047 A1 4/2010 Newman et al.
2013/0065286 A1 3/2013 Medoff et al.
(Continued)

FOREIGN PATENT DOCUMENTS

KR 10-0994594 B1 11/2010
KR 10-1031353 B1 4/2011
(Continued)

OTHER PUBLICATIONS

Suwannakham et al. "Construction and Characterization of ack Knock-Out Mutants of Propionibacterium acidipropionici for Enhanced Propionic Acid Fermentation." *Biotechnology and Bioengineering* 94.2 (2006): 383-395.
(Continued)

*Primary Examiner* — Michael A Salvitti
(74) *Attorney, Agent, or Firm* — NSIP Law

(57) ABSTRACT

The present disclosure relates to a hydrolysate of a mixture of lignocellulosic biomass and seaweed biomass. By mixing seaweed biomass with lignocellulosic biomass and then preparing a hydrolysate, lignocellulosic biomass-derived acetic acid is consumed together with seaweed biomass-derived mannitol. As a result, high sugar productivity can be maintained while reducing fermentation inhibitors. Because the present disclosure can solve the problem of lignocellulosic biomass of decreased fermentation efficiency due to lignocellulose-derived fermentation inhibitors and the problem of seaweed biomass of very low productivity in spite of long fermentation time, the hydrolysate according to the present disclosure may be used to produce biofuels and biochemicals economically.

16 Claims, 12 Drawing Sheets

(51) Int. Cl.
*C12P 19/02* (2006.01)
*C12P 19/12* (2006.01)

(52) U.S. Cl.
CPC ........... *C12P 2203/00* (2013.01); *Y02E 50/17* (2013.01); *Y02E 50/343* (2013.01)

(56) References Cited

U.S. PATENT DOCUMENTS

| | | | | |
|---|---|---|---|---|
| 2013/0209986 A1* | 8/2013 | Um | C12P 7/52 | 435/3 |
| 2014/0004574 A1* | 1/2014 | Medoff | C12P 7/18 | 435/99 |
| 2014/0220640 A1* | 8/2014 | Um | C13K 1/02 | 435/99 |
| 2014/0273108 A1* | 9/2014 | Bleyer | C12P 19/14 | 435/99 |
| 2016/0298146 A1* | 10/2016 | Um | C12P 7/52 | |
| 2017/0130252 A1* | 5/2017 | Medoff | C12P 19/14 | |
| 2017/0130282 A1* | 5/2017 | Eyal | C13K 1/02 | |
| 2017/0159077 A1* | 6/2017 | Medoff | C12P 7/10 | |

FOREIGN PATENT DOCUMENTS

| | | |
|---|---|---|
| KR | 10-2012-0006273 A | 1/2012 |
| KR | 10-2012-0079905 A | 7/2012 |
| KR | 10-2013-0032732 A | 4/2013 |
| KR | 10-1291217 B1 | 7/2013 |
| WO | WO 2013/096693 A1 | 6/2013 |

OTHER PUBLICATIONS

Song, et al. "Butyric Acid Production from Brown Algae Using Clostridium tyrobutyricum ATCC 25755." *Biotechnology and Bioprocess Engineering* 16.1 (2011): 42-49.

Zhang, et al., "Effects of ptb Knock on Butyric Acid Fermentation by Clostridium tyrobutyricum." *Biotechnology Progress* 28.1 (2012): 52-59.

Choi, et al. "Butyrate Production Enhancement by Clostridium tyrobutyricum Using Electron Mediators and a Cathodic Electron Donor." *Biotechnology and Bioengineering* 109.10 (2012): 2494-2502.

Zhou, et al. "Separation of Acetic Acid from Monosaccharides by NF and RO Membranes: Performance Comparison." *Journal of Membrane Science* 429 (2013): 243-251.

Chen, Jingwen, et al. "Removal of Inhibitors From Lignocellulosic Hydrolyzates by Vacuum Membrane Distillation." *Bioresource Technology* 144 (2013): 680-683.

Du, Yinming, et al. "Metabolic Process Engineering of Clostridium tyrobutyricum Δack-adhE2 for Enhanced n-butanol Production from Glucose: Effects of Methyl Viologen on NADH Availability, Flux Distribution, and Fermentation Kinetics." *Biotechnology and Bioengineering* 112.4 (2015): 705-715.

Canganella, Francesco, et al. "Clostridium thermobutyricum: growth studies and stimulation of butyrate formation by acetate supplementation." Microbiological research 157.2 (2002): 149-156. (8 pages in English).

* cited by examiner

HYDROLYSATE OF MIXTURE OF SEAWEED BIOMASS AND LIGNOCELLULOSIC BIOMASS TO IMPROVE BIOCHEMICAL AND BIOFUEL PRODUCTION, AND PREPARATION USING THE SAME

CROSS-REFERENCE TO RELATED APPLICATION

This application claims the priority of Korean Patent Application No. 10-2015-0050321, filed on Apr. 9, 2015, and all the benefits accruing therefrom under 35 U.S.C. § 119, the contents of which in its entirety are herein incorporated by reference.

BACKGROUND

1. Field

The present disclosure relates to a biomass hydrolysate for improving the production efficiency of biochemicals and biofuels, wherein the utilization efficiency of seaweed biomass and lignocellulosic biomass is increased and fermentation inhibitors are reduced, and a method for preparing the same.

DESCRIPTION ABOUT GOVERNMENT-SPONSORED RESEARCH AND DEVELOPMENT

This research was sponsored by the Environmental Convergence Technology Project of the Ministry of Environment supervised by the Korea Institute of Science and Technology (agency of research management: Korea Environmental Industry & Technology Institute, project number: 1485012338). This research was also sponsored by the Korea Institute of Science and Technology (project number: 2E24500).

2. Description of the Related Art

Interests in biofuels that can replace for petroleum resources are increasing in order to resolve the problems of environmental pollution, greenhouse gas emission and depletion of petroleum resources due to the use of fossil fuels. In this regard, researches are being actively carried out on biofuel production from biomass.

The biomass used to produce alternative energy can be largely divided into land biomass and marine biomass. The most widely used biomass is lignocellulosic biomass, which is one of the land biomass and widely used in production of biofuels and biochemicals. However, because cellulose, hemicellulose and lignin are bound complicatedly and tightly, the lignocellulosic biomass should be converted to a fermentable sugar through pretreatment and hydrolysis. Because the pretreatment is conducted under harsh conditions, furan-based compounds and acetic acid generated from overdegradation and phenolic compounds derived from lignin inhibit the growth of and fermentation by microorganisms. As a result, the efficiency of biofuel and biochemical production decreases. Accordingly, for effective fermentation using a hydrolysate of lignocellulosic biomass, removal/reduction of the toxic substances, or detoxification, is necessary.

Among the marine biomass, seaweed biomass is a non-food resource as a third-generation biomass. In Korea, brown algae is produced in the largest quantity. The seaweed biomass such as brown algae is almost free of lignin and fermentation inhibitors are hardly produced because the pretreatment condition is not harsh. But, a small amount of glucose and a large amount of mannitol are produced during the hydrolysis of seaweed biomass. In particular, because mannitol is a more reduced form than a hexose (glucose) or a pentose (xylose, arabinose, etc.) produced from the lignocellulosic biomass, more NADH is produced during the metabolic process. The metabolic consumption and fermentation of mannitol by microorganisms is inhibited by the NADH derived from mannitol because of redox potential imbalance due to high reducing power. For example, Professor Deokjin Jahng et al. at Myongji University (Korea) reported in the production of butyric acid from brown algae using *Clostridium tyrobutyricum* ATCC 25755, the lag phase was quite long (about 120 hours) [1].

REFERENCES OF THE RELATED ART

Non-Patent Documents

[1] Song J-H, Ventura J-R, Lee C-H, Jahng D. Butyric acid production from brown algae using *Clostridium tyrobutyricum* ATCC 25755. *Biotechnology and Bioprocess Engineering* 2011; 16:42-49.

[2] Zhang Y, Yu M, Yang S T. Effects of ptb knockout on butyric acid fermentation by *Clostridium tyrobutyricum. Biotechnology Progress* 2012; 28:52-59.

[3] Suwannakham S, Huang Y, Yang S T. Construction and characterization of ack knock-out mutants of *Propionibacterium acidipropionici* for enhanced propionic acid fermentation. *Biotechnology and Bioengineering* 2006; 94:383-395.

[4] Du Y, Jiang W, Yu M, Tang I, Yang S T. Metabolic process engineering of *Clostridium tyrobutyricum* Δack-adhE2 for enhanced n-butanol production from glucose: Effects of methyl viologen on NADH availability, flux distribution, and fermentation kinetics. *Biotechnology and Bioengineering* 2015; 112:705-715.

[5] Choi O, Um Y, Sang B I. Butyrate production enhancement by *Clostridium tyrobutyricum* using electron mediators and a cathodic electron donor. *Biotechnology and Bioengineering* 2012; 109:2494-2502.

[6] Zhou F, Wang C, Wei J. Separation of acetic acid from monosaccharides by NF and RO membranes: performance comparison. *Journal of Membrane Science* 2013; 429:243-251.

[7] Chen J, Zhang Y, Wang Y, Ji X, Zhang L, Mi X, Huang H. Removal of inhibitors from lignocellulosic hydrolyzates by vacuum membrane distillation. *Bioresource Technology* 2013; 144:680-683.

SUMMARY

In order to solve the problems occurring when a lignocellulosic biomass hydrolysate or a seaweed biomass hydrolysate is used and effectively produce biofuels and biochemicals from biomass through fermentation by microorganisms, the present disclosure is directed to providing a novel hydrolysate resolving the disadvantages of the seaweed biomass and the lignocellulosic biomass, which promotes the growth of microorganisms through consumption of not only fermentable carbon sources but also non-fermentable carbon sources and allows for effective conversion of the carbon sources to metabolites with superior fermentation efficiency.

In an aspect, the present disclosure provides a hydrolysate of a mixture of seaweed biomass and lignocellulosic biomass as a hydrolysate used in fermentation by microorganisms, the hydrolysate being a hydrolysate of biomass which is a mixture of seaweed biomass and lignocellulosic biomass.

In another aspect, the present disclosure provides a hydrolysate of a mixture of seaweed biomass and lignocellulosic biomass as a hydrolysate used in fermentation by microorganisms, the hydrolysate being a mixture of a hydrolysate of seaweed biomass and a hydrolysate of lignocellulosic biomass.

In another aspect, the present disclosure provides a method for preparing the hydrolysate of a mixture of seaweed biomass and lignocellulosic biomass, which includes a mixing step of mixing seaweed biomass and lignocellulosic biomass and a hydrolysis step of hydrolyzing the mixed biomass, or includes a hydrolysis step of hydrolyzing seaweed biomass and lignocellulosic biomass independently and a mixing step of mixing the hydrolyzed seaweed biomass and the hydrolyzed lignocellulosic biomass.

In another aspect, the present disclosure provides a method for producing a biochemical or a biofuel, which includes a fermentation step of adding the hydrolysate of a mixture of seaweed biomass and lignocellulosic biomass prepared by the above-described method to microorganisms and fermenting the same by culturing the microorganisms.

The combination of a seaweed biomass hydrolysate and a lignocellulosic biomass hydrolysate according to the present disclosure causes simultaneous consumption of seaweed biomass-derived mannitol and lignocellulosic biomass-derived acetic acid during fermentation and enables effective consumption of mannitol. Through this, the problem of slow mannitol consumption occurring when fermentation occurs only with the seaweed biomass hydrolysate and the problem of carbon loss due to the formation of by-product such as acetic acid occurring when fermentation occurs only with the lignocellulosic biomass hydrolysate may be solved. More surprisingly, in accordance with the present disclosure, a higher fermentation efficiency may be achieved because effective fermentation is possible using the lignocellulosic biomass-derived sugar and the acetic acid along with the seaweed biomass-derived mannitol at the same time. Also surprisingly, any detoxification process is not necessary because the combination of a seaweed biomass hydrolysate and a lignocellulosic biomass hydrolysate according to the present disclosure contains less lignocellulosic biomass and the production of fermentation inhibitors can be reduced.

Accordingly, the present disclosure can solve the problem of seaweed biomass of very low productivity in spite of long fermentation time and the problem of lignocellulosic biomass of decreased fermentation efficiency due to lignocellulose-derived fermentation inhibitors. Therefore, the hydrolysate according to the present disclosure may be used to produce biofuels and biochemicals economically.

DETAILED DESCRIPTION

Figure 1:
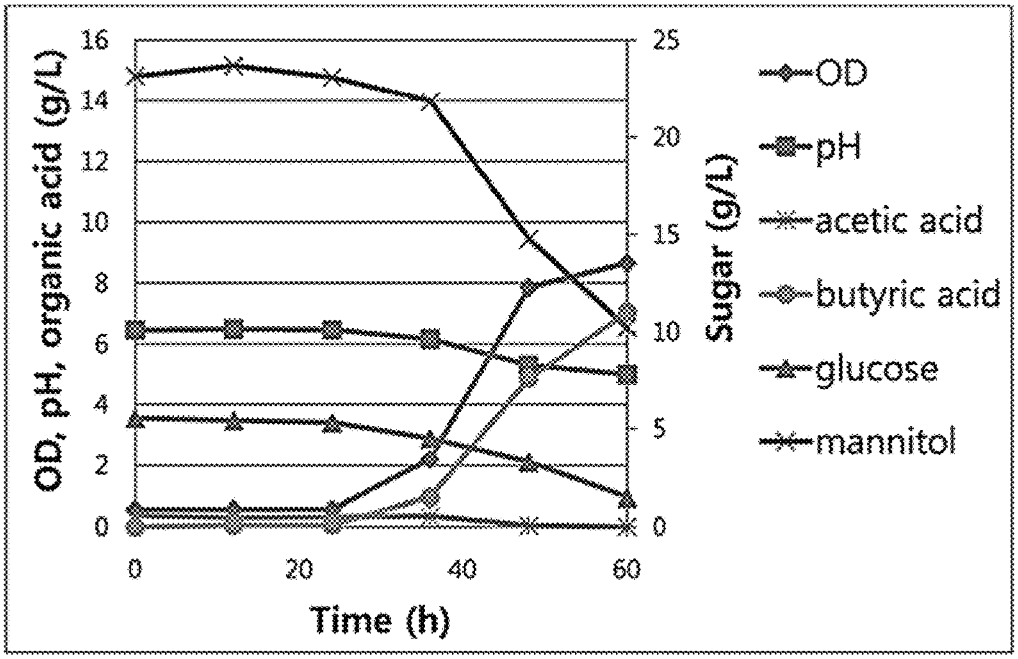
FIG. 1 shows a result of analyzing the fermentation pattern of *Clostridium tyrobutyricum* ATCC 25755 when a hydrolysate prepared from seaweed biomass is used.

In the present disclosure "biomass" refers to a biological material derived from land plants, seaweeds, microalgae, microorganisms, etc. that can be used as an energy source, and "biochemical" refers to any chemical material that can be obtained by thermally/chemically degrading or fermenting the biomass. And, "biofuel" refers to a fuel derived from the biomass and is used in the broadest concept, including not only bioalcohol and biooil but all metabolites that can be converted to fuel through chemical or biological techniques.

Hereinafter, the present disclosure is described in detail.

In an aspect, the present disclosure provides a hydrolysate of a mixture of seaweed biomass and lignocellulosic biomass as a hydrolysate used in fermentation by microorganisms. In another aspect, the present disclosure provides a hydrolysate which is a mixture of a hydrolysate of seaweed biomass and a hydrolysate of lignocellulosic biomass as a hydrolysate used in fermentation by microorganisms. Hereinafter, both of the above two biomass hydrolysates are referred to as a "hydrolysate of a mixture of seaweed biomass and lignocellulosic biomass".

In an exemplary embodiment of the present disclosure, the lignocellulosic biomass usually consists of lignocellulose which is a composite composed of cellulose, hemicellulose, lignin, etc. Specifically, the lignocellulosic biomass contains 33-51 wt % of cellulose, 19-34 wt % of hemicellulose, 21-32 wt % of lignin, 0-2 wt % of ash as well as other trace components. The lignocellulosic biomass is not limited to whether it is derived from a conifer or a broadleaf, the species of the tree from which it is derived, the age of the tree, etc. as long as it is a biological material containing lignocellulose. For example, it may include softwood derived from trees, softwood chips, slash or hog fuel obtained by processing softwood, forest residues, straw such as rice straw, chaff, grain, grass, corn, corn husks, weeds, aquatic plants, hay, etc.

Because cellulose, hemicellulose and lignin are complicatedly bound to each other in the lignocellulosic biomass, pretreatment and hydrolysis processes under harsh environments are necessary to make it into monosaccharides that can be used by microorganisms. During these processes, the cellulose and the hemicellulose are hydrolyzed to pentoses or hexoses including glucose, galactose, mannose, rhamnose, xylose and arabinose. Also, furan-based compounds such as furan, hydroxymethylfurfural (HMF) and furfural, acetic acid, etc. are produced due to overdegradation of the sugars. The lignin is hydrolyzed to phenolic compounds such as ferulic acid, coumaric acid, benzoic acid, syringic acid, vanillic acid, vanillin, 4-hydroxybenzoic acid, 4-hydroxybenzaldehyde, syringaldehyde, etc.

Among the compounds produced from the hydrolysis of the lignocellulosic biomass, the phenolic compounds, the furan-based compounds, etc. act as fermentation inhibitors which inhibit the growth of microorganisms and decrease the production efficiency of biochemicals or biofuels. Especially, because 10 wt % or more of the lignocellulosic biomass is not fermented by microorganisms due to the fermentation inhibitors, a process for removing or reducing them is necessary.

The seaweed biomass according to an exemplary embodiment of the present disclosure exhibits short production cycle and remarkably superior productivity per unit area as compared to the land biomass. Also, it is advantageous in that hydrolysis is relatively easy because it does not contain lignin. The seaweed biomass may be, for example, red algae, brown algae, green algae, etc., although not being limited thereto. It includes those harvested directly from the sea or aquacultured ones. Mannitol can be produced in large quantities from hydrolysis of the brown algae, which are produced in large amounts in Korea. Examples include tangle (*Laminaria japonica*), wakame (*Undaria pinnatifida*), hijiki (*Hizikia fusiforme*), sea fir (*Analipus japonicus*), *Chordaria flagelliformis, Ishige okamurai, Scytosiphon lomentaria, Endarachne binghamiae, Ecklonia cava, Ecklonia stolonifera*, sea oak (*Eisenia bicyclis*), *Costaria costata*, gulfweed (*Sargassum fulvellum*), *Sargassum horner*), *Sargassum thunbergii*, etc. Examples of the red algae include agar (*Gelidium amansii*), *Bangia atropurpurea, Porphyra suborbiculata, Porphyra yezoensis, Galaxaura falcata, Scinaia japonica, Gelidium divaricatum, Gelidium pacificum, Lithophylum okamurae, Lithothammion cystocarpideum, Amphiroa anceps, Amphiroa beauvoisii, Corallina officinalis, Corallina pilulifera, Marginisporum aberrans, Carpopeltis prolifera, Grateloupia filicina, Grateloupia elliptica, Grateloupia lanceolanta, Grateloupia turtuturu, Phacelocarpus japonicus*, glueweed (*Gloiopeltis furcata*), *Hypnea charoides, Hypnea japonitca, Hypnea saidana*, carrageen moss (*Chondrus cripspus*), *Chondracanthus tenellus, Gracilaria textorii, Lomentaria catenata, Heterosiphonia japonica, Chondria crassicaulis, Symphyocladia latiuscula*, laver (*Porphyra yezoensis* Ueda), *Kappaphycus cottonii, Grateloupia lanceolata, Pterocladia tenuis, Acanthopeltis japonica, Gloiopeltis tenax*, Irish moss, *Pachymeniopsis elliptica, Ceramium kondoi, Ceramium boydenii, Gigartina tenella, Campylaephora hypnaeoides*, etc. Examples of the green algae include green laver (*Enteromorpha*), sea lettuce (*Ulva lactuca*), water silk (*Spirogyra* spp.), green sea fingers (*Codium fragile*), *Codium minus, Caulerpa okamurae*, star jelly (*Nostoc commune*), etc.

The seaweed biomass according to an exemplary embodiment contains polysaccharides such as alginic acid and laminaran as well as the carbohydrate mannitol. Mannitol is a sugar which is more reduced as compared to glucose that produces two NADHs. Therefore, it can be used to produce bioalcohols and biochemicals as it produces three NADHs per molecule when it is converted to pyruvic acid through glycolysis. Also, the seaweed biomass is advantageous in that hydrolysis is relatively easy because it does not contain lignin and the seaweed biomass hydrolysate has low toxicity as compared to the lignocellulosic biomass hydrolysate because it is almost free from the highly toxic phenolic compounds derived from lignin.

However, there is a problem in that there are relatively few microorganisms that can degrade the sugars present mainly in the seaweed, such as galactose or mannitol, and that, if the NADHs produced from the glucose and mannitol cannot be consumed effectively, the growth of and fermentation by the microorganisms are inhibited because of redox potential imbalance due to high reducing power.

The embodiments of the present disclosure show that, if a mixture of seaweed biomass and lignocellulosic biomass is hydrolyzed or a seaweed biomass hydrolysate and a lignocellulosic biomass hydrolysate are mixed, the fermentation efficiency of mannitol is increased as the lignocellulosic biomass-derived acetic acid and the seaweed biomass-derived mannitol are consumed together. Accordingly, the mixed hydrolysate according to the present disclosure can be used to convert not only fermentable carbon sources derived from seaweed biomass and lignocellulosic biomass but also non-fermentable carbon sources such as acetic acid and butyric acid to metabolites.

Also, the hydrolysate according to an exemplary embodiment of the present disclosure is advantageous in that the used amount of lignocellulosic biomass can be reduced because seaweed biomass is used together with the lignocellulosic biomass. As a result, the mixed biomass hydrolysate may contain 50-100 wt % less fermentation inhibitors as compared to a lignocellulosic biomass hydrolysate with the same amount as the total weight of the seaweed biomass and the lignocellulosic biomass in the hydrolysate based on the total volume of the hydrolysate. If the fermentation inhibitors are reduced less than 50 wt % as compared to a lignocellulosic biomass hydrolysate with the same amount as the total weight of the seaweed biomass and the lignocellulosic biomass, the fermentation inhibitors may inhibit fermentation because the concentration thereof is not low enough. More specifically, the hydrolysate of a mixture of seaweed biomass and lignocellulosic biomass may contain 60 wt %, 70 wt %, 80 wt %, 85 wt % 90 wt % or 100 wt % less fermentation inhibitors as compared to a lignocellulosic biomass hydrolysate with the same amount as the total weight of the seaweed biomass and the lignocellulosic biomass in the hydrolysate based on the total volume of the hydrolysate. Herein, the weight of the seaweed biomass may be dry weight.

In an exemplary embodiment, the fermentation inhibitor may contain one or more of a phenolic compound and a furan-based compound. For example, the fermentation inhibitor may include: one or more phenolic compound selected from a group consisting of ferulic acid, coumaric acid, benzoic acid, syringic acid, vanillic acid, vanillin, 4-hydroxybenzoic acid, 4-hydroxybenzaldehyde and syringaldehyde; and one or more furan-based compound selected from a group consisting of furan, furfural and 5-hydroxymethylfurfural (5-HMF), although not being limited thereto.

The hydrolysate of a mixture of seaweed biomass and lignocellulosic biomass according to an exemplary embodiment of the present disclosure may contain 75-100 wt % of a sugar as compared to a lignocellulosic biomass hydrolysate with the same amount as the total weight of the seaweed biomass and the lignocellulosic biomass in the hydrolysate based on the total volume of the hydrolysate. The sugar may be one or more selected from: one or more monosaccharide selected from a group consisting of glucose, galactose, mannose, rhamnose, xylose and arabinose; cellobiose as a disaccharide; and one or more polysaccharide selected from a group consisting of mannitol, alginic acid and laminaran, although not being limited thereto. More specifically, the hydrolysate may contain mannitol and glucose when the seaweed biomass is tangle biomass or gulfweed biomass, and the hydrolysate may contain mannose, galactose, xylose and arabinose when the seaweed biomass is agar biomass or sea lettuce biomass.

In an exemplary embodiment of the present disclosure, the hydrolysate of a mixture of seaweed biomass and lignocellulosic biomass may have a weight ratio of seaweed biomass and lignocellulosic biomass of 9:1-1:9. Or, the mixture of the hydrolysate of seaweed biomass and the hydrolysate of lignocellulosic biomass may have a weight ratio of seaweed biomass and lignocellulosic biomass of 9:1-1:9. More specifically, the weight ratio of seaweed biomass and lignocellulosic biomass may be 9:1-5:5 or 7.5-8.5:1.5-2.5.

Because the amount of lignocellulosic biomass with high toxicity due to phenolic compounds, etc. in the mixed biomass can be decreased from 10% (w/v) to, e.g., 1-3%, the production of lignocellulosic biomass-derived fermentation inhibitors can be reduced and, accordingly, an additional process of removing/detoxifying the fermentation inhibitors is unnecessary. In addition, the mannitol contained in the hydrolysate of seaweed biomass is consumed rapidly with high fermentation efficiency if acetic acid is produced as lignocellulosic biomass is hydrolyzed. The mannitol derived from seaweed biomass is an unfavored sugar which is not easily consumed by microorganisms because it has high reducing power as compared to glucose which is fermented by most microorganisms. In the present disclosure, the acetic acid present in the lignocellulosic biomass hydrolysate allows for effective fermentation of mannitol by playing an important role in redox potential balancing in microorganisms. That is to say, as demonstrated in the following examples of the present disclosure, the production yield of biochemicals or biofuels can be improved because the unfavored sugar mannitol can be fermented effectively as acetic acid is consumed.

In another aspect, the present disclosure provides a method for preparing the hydrolysate of a mixture of seaweed biomass and lignocellulosic biomass, which includes a mixing step of mixing seaweed biomass and lignocellulosic biomass and a hydrolysis step of hydrolyzing the mixed biomass. In another aspect, the present disclosure provides a method for preparing the hydrolysate of a mixture of seaweed biomass and lignocellulosic biomass, which includes a hydrolysis step of hydrolyzing seaweed biomass and lignocellulosic biomass independently and a mixing step of mixing the hydrolyzed seaweed biomass and lignocellulosic biomass. The two preparation methods are different only in the order of the mixing step and the hydrolysis step, and the mixed biomass hydrolysates prepared by the two methods are identical in constitution and provide the same effects. In an exemplary embodiment, the method which includes a mixing step of mixing seaweed biomass and lignocellulosic biomass and a hydrolysis step of hydrolyzing the mixed biomass may be employed when the two types of biomass have similar pretreatment and hydrolysis conditions. In another exemplary embodiment, the method which includes a hydrolysis step of hydrolyzing seaweed biomass and lignocellulosic biomass independently and a mixing step of mixing the hydrolyzed seaweed biomass and lignocellulosic biomass may be employed when the two types of biomass have different pretreatment and hydrolysis conditions.

In an exemplary embodiment of the present disclosure, the two preparation methods may further include, before the hydrolysis step, a pretreatment step for softening the seaweed biomass and the lignocellulosic biomass. In an exemplary embodiment, the step of pretreating the mixed biomass may include one or more of chemically treating with an acid, a base, etc., e.g., dilute sulfuric acid, physically treating with high temperature, high pressure, etc. or biologically treating with an enzyme, a microorganism, etc., although not being limited thereto, in order to soften the hard lignocellulosic biomass so that the high-molecular-weight sugars in the lignocellulosic biomass can be easily hydrolyzed before they are hydrolyzed to low-molecular-weight sugars that can be used by microorganisms.

In another aspect, the present disclosure provides a method for preparing a biochemical or a biofuel, which includes a fermentation step of adding the hydrolysate of a mixture of seaweed biomass and lignocellulosic biomass prepared by the above-described method to microorganisms and fermenting the same by culturing the microorganisms.

In an exemplary embodiment, in a hydrolysis step, as sugars are produced from seaweed biomass and lignocellulosic biomass, a reduced amount of fermentation inhibitors may be produced as compared to when the lignocellulosic biomass is hydrolyzed alone. In the hydrolysis step, sugars including mannitol may be produced from the seaweed biomass and acetic acid may be produced from the lignocellulosic biomass. During the fermentation step, the fermentation may occur as the mannitol and the acetic acid are consumed together.

In an exemplary embodiment, the fermentation step may be accomplished by microorganisms added to the hydrolysate. The microorganism may be selected in consideration of fermentation capability for sugars, resistance to fermentation inhibitors that may be present in the hydrolysate, etc.

The microorganism used in the fermentation includes any microorganism commonly used in fermentation. Specifically, one or more selected from yeast, *Lactobacillus, Clostridium, E. coli* and *Bacillus* may be used either in combination or alone. More specifically, the microorganism may be one or more selected from a group consisting of *Anaeromyxobacter* sp., *Alcaligenes* sp., *Bacteroides* sp., *Bacillus* sp., *Clostridium* sp., *Escherichia* sp., *Lactobacillus* sp., *Lactococcus* sp., *Pichia* sp., *Pseudomonas* sp., *Ralstonia* sp., *Rhodococcus* sp., *Saccharomyces* sp., *Streptomyces* sp., *Thermus* sp., *Thermotoga* sp., *Thermoanaerobacter* sp. and *Zymomonas* sp., although not being limited thereto. More specifically, the microorganism may be one or more selected from a group consisting of *Clostridium beijerinckii, Clostridium acetobutyricum, Clostridium butyricum, Clostridium cellulolyticum, Clostridium thermocellum, Clostridium perfingens, Clostridium sprorogenes, Clostridium thermohydrosulfuricum, Clostridium kluyveri, Clostridium aciditolerans, Clostridium pasteurianum, Clostridium ljungdahlii, Clostridium autoethanogenum, Clostridium formicoacticum, Clostridium thermoaceticum, Clostridium aceticum* and *Clostridium tyrobutyricum*, although not being limited thereto.

In an exemplary embodiment, the biochemical or the biofuel prepared by the above-described method may be different depending on the particular microorganism. The biochemical may be one or more of a fatty acid, a diol, a diene and an organic acid. Specifically, the organic acid may be, for example, lactic acid, acetic acid, butyric acid, hexanoic acid, etc., and the biofuel may be, for example, acetone, ethanol, butanol, etc.

Hereinafter, the present disclosure will be described in detail through examples. However, the following examples are for illustrative purposes only and it will be apparent to those of ordinary skill in the art that the scope of the present disclosure is not limited by the examples.

[Test Example 1] Analysis of Organic Acid Fermentation Efficiency of Lignocellulosic or Seaweed Biomass Hydrolysate In order to investigate the fermentation efficiency of a hydrolysate depending on the type of biomass, hydrolysates were prepared by pretreating and hydrolyzing seaweed biomass and lignocellulosic biomass respectively. Tangle biomass was used as the seaweed biomass and rice straw biomass was used as the lignocellulosic biomass.

Specifically, each biomass was pretreated at 121° C. for 30 minutes by adding to a 1.5% sulfuric acid (w/v) aqueous solution to a concentration of 10% (w/v). After adjusting pH to 5.0 using calcium hydroxide for hydrolysis of the pretreated biomass, a hydrolysate was prepared by enzymatically hydrolyzing the biomass at 50° C. for 2 days by adding 1 mL of cellulase per 100 g of the biomass. *Clostridium tyrobutyricum* ATCC 25755 (American Type Culture Collection) was used for fermentation of butyric acid from the hydrolysate.

The seaweed biomass hydrolysate (Comparative Example 1) contained 6.2 g of glucose, 25.3 g of mannitol and 0.2 g of acetic acid per liter. And, the lignocellulosic biomass hydrolysate (Comparative Example 2) contained 26.6 g of glucose, 14.6 g of xylose, 1.02 g of acetic acid and 0.9 g phenolic compounds per liter.

For fermentation of butyric acid, 5 g of yeast extract, 0.2 g of magnesium sulfate, 0.01 g of manganese sulfate, 0.01 g of iron sulfate, 0.01 g of sodium chloride, 0.5 g of monopotassium phosphate ($KH_2PO_4$), 0.5 g of dipotassium phosphate ($K_2HPO_4$) and 2 g of ammonium sulfate were added to 1 L of the seaweed biomass hydrolysate (Comparative Example 1) or the lignocellulosic biomass hydrolysate (Comparative Example 2). After adding 100 mM MES (2-(N-morpholino)ethanesulfonic acid) to prevent excessive decrease of pH due to the production of organic acids, initial pH was adjusted to 6.8 using 6 N potassium hydroxide (KOH). For batch culture, after adding 20 mL of a medium to a 60-mL serum bottle and then inoculating 2.5% of culture, culturing was conducted at 37° C. and 150 rpm in a shaking incubator.

The concentration of sugars and organic acids was measured for each culture. The concentration was analyzed by liquid chromatography (Agilent model 1200 liquid chromatograph). The sugars and butyric acid were analyzed using a refractive index detector and a Hi-Plex H column (300×7.8 mm, Agilent). The growth of microorganisms was analyzed by measuring absorbance at 600 nm using a spectrophotometer (UVmini-1240, Shimadzu).

FIG. 1 shows a result of observing the organic acid fermentation pattern of *Clostridium tyrobutyricum* ATCC 25755 for the seaweed biomass hydrolysate (Comparative Example 1). It can be seen that the growth of the microorganisms and the production of organic acids were observed only after 24 hours of fermentation. After 60 hours of fermentation, 7 g/L butyric acid was produced from 4 g/L glucose and 12.9 g/L mannitol. When *Clostridium tyrobutyricum* ATCC 25755 was cultured using the seaweed biomass only, the fermentation efficiency was very low because the lag phase was very long and all the sugars contained in the hydrolysate were not used.

Figure 2:
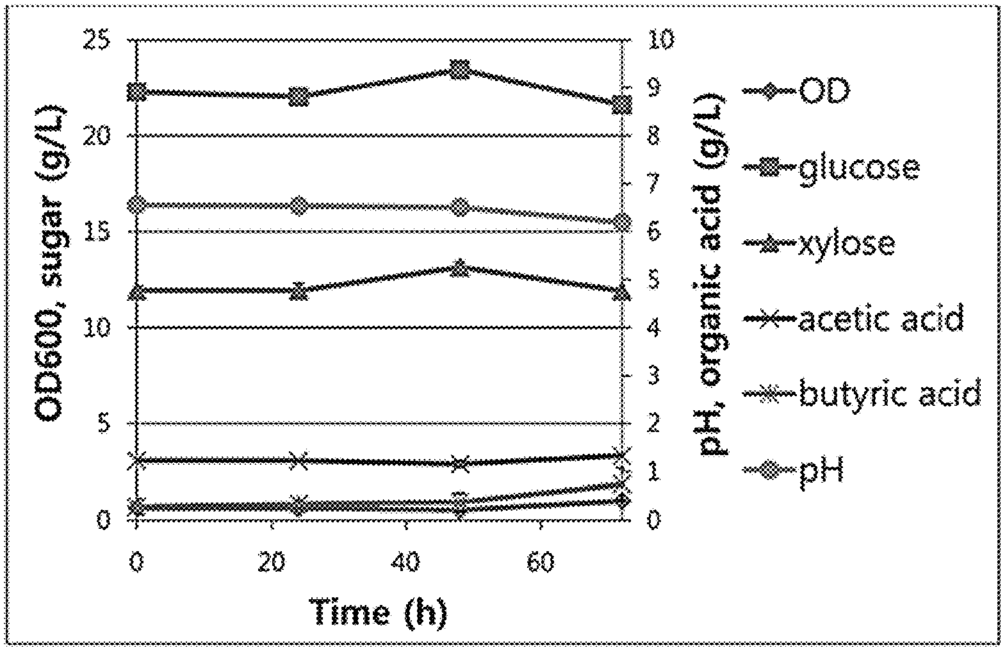
FIG. 2 shows a result of analyzing the fermentation pattern of *Clostridium tyrobutyricum* ATCC 25755 when a hydrolysate prepared from lignocellulosic biomass is used.

FIG. 2 shows a result of observing the organic acid fermentation pattern of *Clostridium tyrobutyricum* ATCC 25755 for the lignocellulosic biomass hydrolysate (Comparative Example 2). It can be seen that the growth of the microorganisms and the production of organic acids were hardly observed until 72 hours of fermentation.

This result suggests that, among the compounds produced from the hydrolysis of the lignocellulosic biomass, phenolic compounds, weak acids, etc. act as fermentation inhibitors which decrease the production efficiency of biochemicals such as organic acids or biofuels through fermentation by microorganisms. Unless the fermentation inhibitors are removed or reduced, the fermentation efficiency of 10 wt % or higher lignocellulosic biomass hydrolysate remains low as in this experiment. Also, the hydrolysate of seaweed biomass exhibits very low production efficiency of biochemicals such as organic acids or biofuels due to long fermentation time and low mannitol degradability.

Accordingly, it can be seen that the hydrolysate prepared from the seaweed or lignocellulosic biomass alone is not suitable for fermentation of organic acids and will provide low production efficiency of biofuels or biochemicals in fermentation by microorganisms.

[Test Example 2] Analysis of Fermentation Efficiency of Seaweed Biomass Hydrolysate Depending on Addition of Acetic Acid The following experiment was conducted to compare the fermentation efficiency depending on addition of acetic acid to the seaweed biomass hydrolysate.

First, in order to analyze the mannitol consumption pattern in organic acid fermentation, 0, 2.5 or 5 g/L sodium acetate was added to a medium containing 27 g of mannitol, 5 g of yeast extract, 0.2 g of magnesium sulfate, 0.01 g of manganese sulfate, 0.01 g of iron sulfate, 0.01 g of sodium chloride, 0.5 g of monopotassium phosphate ($KH_2PO_4$), 0.5 g of dipotassium phosphate ($K_2HPO_4$) and 2 g of ammonium sulfate per liter. After adding 100 mM MES (2-(N-morpholino)ethanesulfonic acid) to prevent excessive decrease of pH due to the production of organic acids, initial pH was adjusted to 6.8 using 1 N potassium hydroxide (KOH). For batch culture, after adding 20 mL of a medium to a 60-mL serum bottle and then inoculating 2.5% of culture, culturing was conducted at 37° C. and 150 rpm in a shaking incubator. *Clostridium tyrobutyricum* ATCC 25755 (American Type Culture Collection) was used for fermentation of butyric acid.

The concentrations of mannitol and organic acids were measured for each culture. The concentrations were analyzed by liquid chromatography (Agilent model 1200 liquid chromatograph). The mannitol and butyric acid were analyzed using a refractive index detector and a Hi-Plex H column (300×7.8 mm, Agilent). The growth of microorganisms was analyzed by measuring absorbance at 600 nm using a spectrophotometer (UVmini-1240, Shimadzu).

Figure 3A:
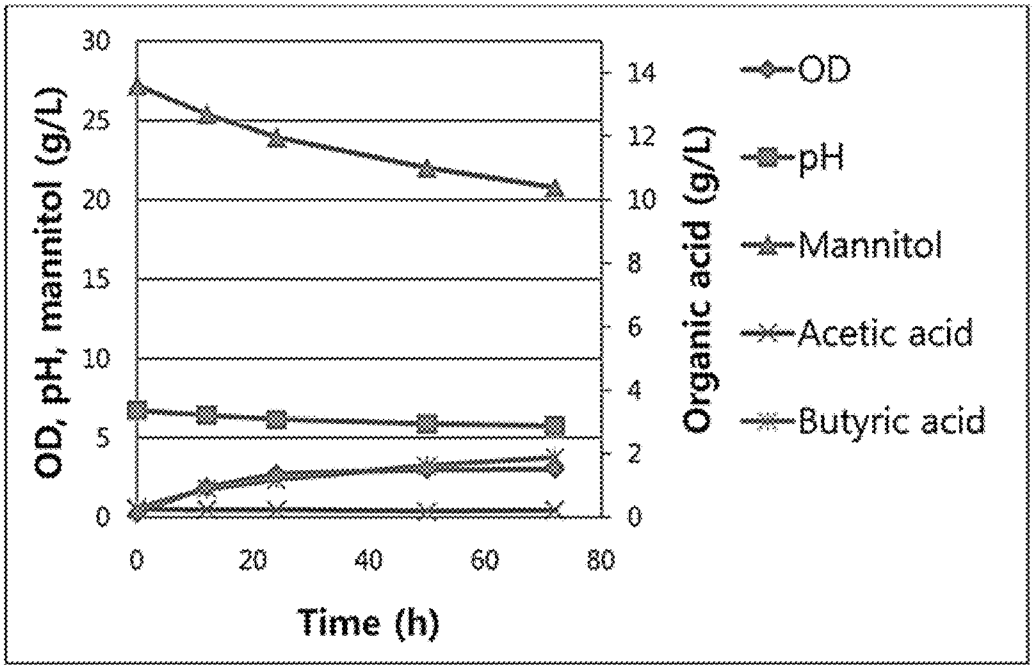
FIGS. 3*a*-3*c* show a result of analyzing the fermentation pattern of *Clostridium tyrobutyricum* ATCC 25755 when fermenting seaweed biomass-derived mannitol depending on the addition of acetic acid (FIG. 3*a*: acetic acid not added, FIG. 3*b:* 2.5 g/L acetic acid added, FIG. 3*c:* 5 g/L acetic acid added).
Figure 3B:
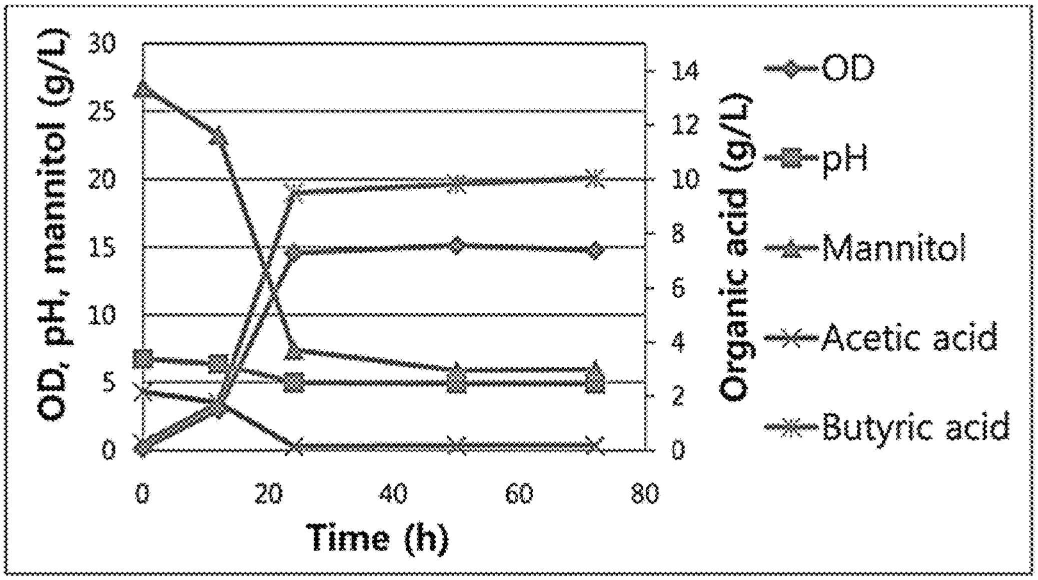
Figure 3C:
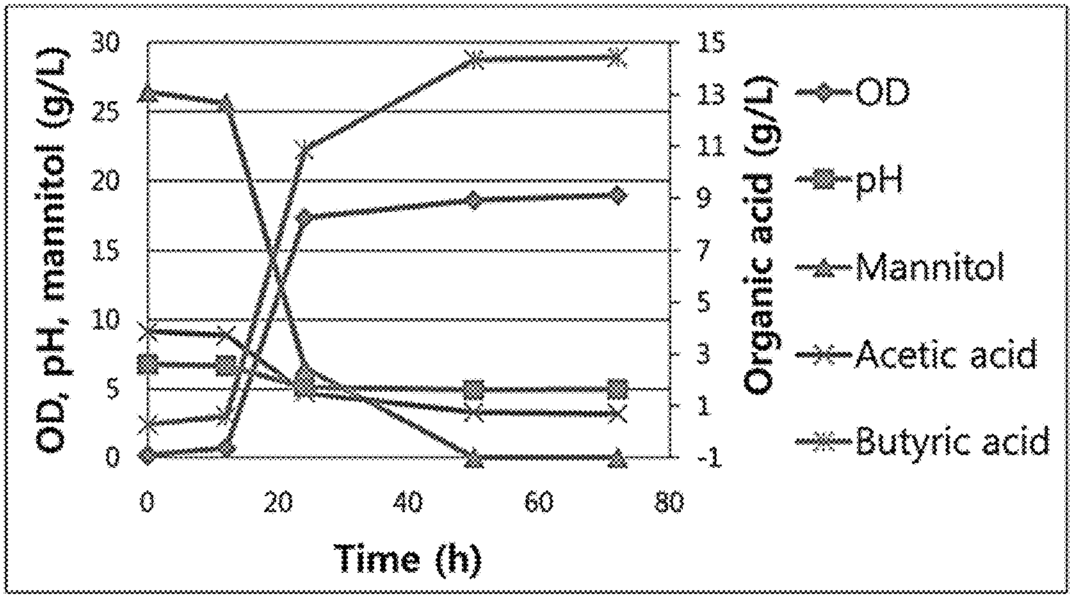

FIG. **3*a* shows a result when sodium acetate was not added. It can be seen that 6.5 g of mannitol was consumed and 1.9 g of butyric acid was produced per liter for 72 hours. FIG. 3*b*** shows the growth of the microorganisms and the production of organic acid when 2.5 g of sodium acetate was added per liter. It can be seen that 9.8 g of butyric acid was produced from 20.8 g of mannitol produced per liter for 72 hours. From the fact that the consumption of mannitol became quite slow from 24 hours when the acetic acid in the medium was depleted, it can be seen that the microorganisms could not consume mannitol due to high reducing power. FIG. 3c shows the growth of the microorganisms and the production of organic acid when 5 g of sodium acetate was added per liter. It can be seen that all the mannitol (26.5 g/L) contained in the medium was consumed and 14.4 g/L of butyric acid was produced. That is to say, it can be seen that the redox imbalance caused by mannitol is resolved by the consumption of acetic acid, thereby leading to consumption of mannitol.

From this result, it can be seen that acetic acid is necessary for redox balancing for effective fermentation of mannitol contained in the seaweed biomass hydrolysate.

Based on the experimental result, a hydrolysate was prepared by pretreating 121° C. at for 30 minutes and hydrolyzing tangle biomass as seaweed biomass after adding a 1.5% sulfuric acid (w/v) aqueous solution to a concentration of 10% (w/v). The seaweed biomass hydrolysate contained 28.4 g of mannitol and 0.2 g of acetic acid per liter.

After adjusting pH to 6.5 using calcium hydroxide for hydrolysis of the pretreated biomass, 5 g of yeast extract, 0.2 g of magnesium sulfate, 0.01 g of manganese sulfate, 0.01 g of iron sulfate, 0.01 g of sodium chloride, 0.5 g of monopotassium phosphate ($KH_2PO_4$), 0.5 g of dipotassium phosphate ($K_2HPO_4$), 2 g of ammonium sulfate and 5 g of sodium acetate were added per liter. For batch culture, after adding 20 mL of a medium to a 60-mL serum bottle and then inoculating 2.5% of culture, culturing was conducted at 37° C. and 150 rpm. *Clostridium tyrobutyricum* ATCC 25755 (American Type Culture Collection) was used for fermentation of butyric acid.

Figure 4:
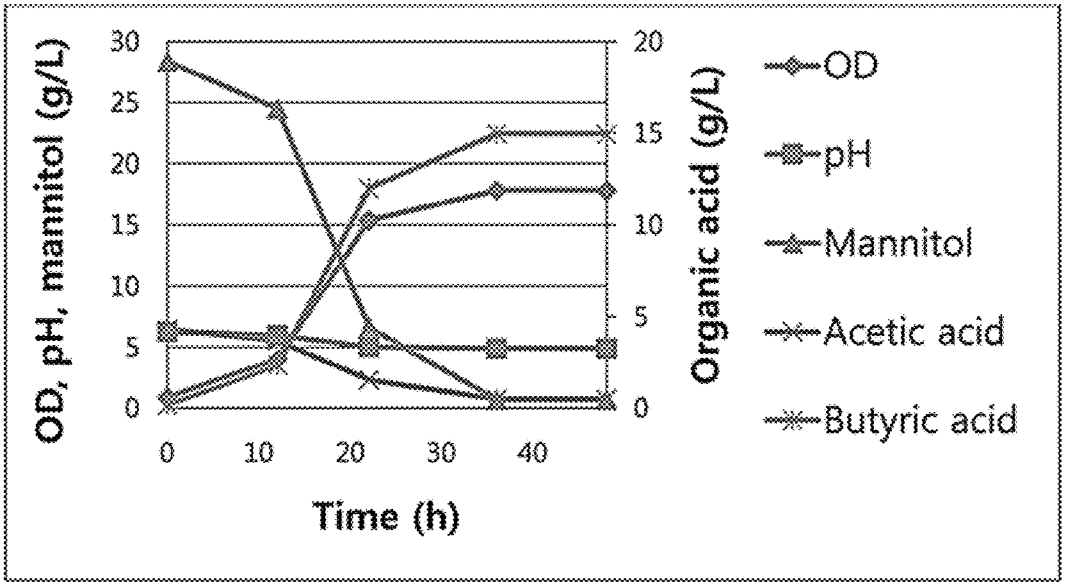
FIG. 4 shows a result of analyzing the increase in fermentation efficiency of *Clostridium tyrobutyricum* ATCC 25755 for seaweed biomass hydrolysate depending on the addition of acetic acid.

As seen from FIG. 4, when fermentation was conducted by adding acetic acid to the seaweed biomass hydrolysate, butyric acid (15 g/L) was produced as mannitol (27.7 g/L) and acetic acid (3.8 g/L) in the hydrolysate were consumed together.

*Clostridium tyrobutyricum*, which is used the most widely in the production of butyric acid using microorganisms, produces not only butyric acid but also acetic acid. The production of acetic acid is problematic in that the production yield of the target product butyric acid is decreased. Therefore, researches have been conducted on the interruption of metabolic pathway to acetic acid through gene manipulation to focus the carbon flow from the substrate to butyric, in order to prevent this problem [2, 3]. Also, researches have been conducted on the supply of a chemical reducing agent such as methylviologen from outside [4] or the supply of reducing power via electrochemical means [5].

In accordance with the present disclosure, the metabolic flow of carbon can be focused to the target product by using the biomass-derived substrate with high reducing power, without the complicated gene manipulation or the supply of chemicals or energy from outside. In addition, because it was confirmed that acetic acid derived from the lignocellulosic biomass can be useful in resolving the redox potential imbalance, it can be seen that the fermentation efficiency of the biomass hydrolysate may be improved by mixing seaweed biomass with lignocellulosic biomass.

[Test Example 3] Analysis of Fermentation Efficiency of Hydrolysate of Mixture of Seaweed Biomass and Lignocellulosic Biomass 1

As demonstrated in Test Examples 1 and 2, the lignocellulosic biomass hydrolysate cannot be used for fermentation by microorganisms unless the fermentation inhibitors are removed because of high toxicity. Also, effective fermentation is not possible with the seaweed biomass because of high reducing power of mannitol.

In this example, a hydrolysate of a mixed biomass of seaweed biomass and lignocellulosic biomass was prepared as an exemplary embodiment of the present disclosure and the improvement in fermentation efficiency was analyzed.

First, 10% (w/v) of a mixed biomass wherein seaweed biomass (tangle) and lignocellulosic biomass (rice straw) were mixed at a weight ratio of 9:1, 8:2 or 7:3 and pretreated at 121° C. for 30 minutes by adding the mixture to a 1.5% (w/v) sulfuric acid aqueous solution. After adjusting pH to 5.0 using calcium hydroxide for hydrolysis of the pretreated biomass, a hydrolysate was prepared by enzymatically hydrolyzing the biomass at 50° C. for 2 days by adding 1 mL of cellulase per 100 g of the biomass. The composition of the prepared hydrolysate is summarized in Table 1.

TABLE 1

|  | Seaweed biomass, % (w/v) | Lignocellulosic biomass, % (w/v) |  | Glucose | Xylose | Mannitol | Acetic acid | Total phenolics |
|---|---|---|---|---|---|---|---|---|
| Comp. Ex. 1 | 10 | 0 | Conc. (g/L) | 6.16 | 0 | 25.3 | 0.22 | N.D. |
| Comp. Ex. 2 | 0 | 10 |  | 26.58 | 14.64 | 0 | 1.02 | 0.87 |
| Ex. 1 | 9 | 1 |  | 7.45 | 1.8 | 22.85 | 0.27 | N.D. |
| Ex. 2 | 8 | 2 |  | 8.97 | 2.68 | 20.59 | 0.45 | 0.19 |
| Ex. 3 | 7 | 3 |  | 10.5 | 3.45 | 17.54 | 0.56 | 0.24 |

As can be seen from Table 1, whereas 0.87 g/L phenolic compounds were produced as fermentation inhibitors for the lignocellulosic biomass hydrolysate of Comparative Example 2, the hydrolysates of the mixtures of lignocellulosic biomass and seaweed biomass of Examples 1-3 showed significantly decreased phenolic compounds. Also, the hydrolysates of Examples 1-3 are thought to exhibit high fermentation efficiency than those of Comparative Examples 1 and 2 prepared from single biomass because acetic acid is consumed together during fermentation of mannitol produced from the seaweed biomass.

Next, fermentation was conducted for each hydrolysate using *Clostridium tyrobutyricum* ATCC 25755 (American Type Culture Collection). For the fermentation, 5 g of yeast extract, 0.2 g of magnesium sulfate, 0.01 g of manganese sulfate, 0.01 g of iron sulfate, 0.01 g of sodium chloride, 0.5 g of monopotassium phosphate ($KH_2PO_4$), 0.5 g of dipotassium phosphate ($K_2HPO_4$) and 2 g of ammonium sulfate per liter were added to the hydrolysate. After adding 100 mM MES (2-(N-morpholino)ethanesulfonic acid) to prevent excessive decrease of pH due to the production of organic acids, initial pH was adjusted to 6.8 using 6 N potassium hydroxide (KOH). For batch culture, after adding 20 mL of a medium to a 60-mL serum bottle and then inoculating 2.5% of culture, culturing was conducted at 37° C. and 150 rpm in a shaking incubator.

The concentration of sugars and organic acids was measured for each culture. The concentration was analyzed by liquid chromatography (Agilent model 1200 liquid chromatograph). The sugars and butyric acid were analyzed using a refractive index detector and a Hi-Plex H column (300×7.8 mm, Agilent). The growth of microorganisms was analyzed by measuring absorbance at 600 nm using a spectrophotometer (UVmini-1240, Shimadzu).

Figure 5A:
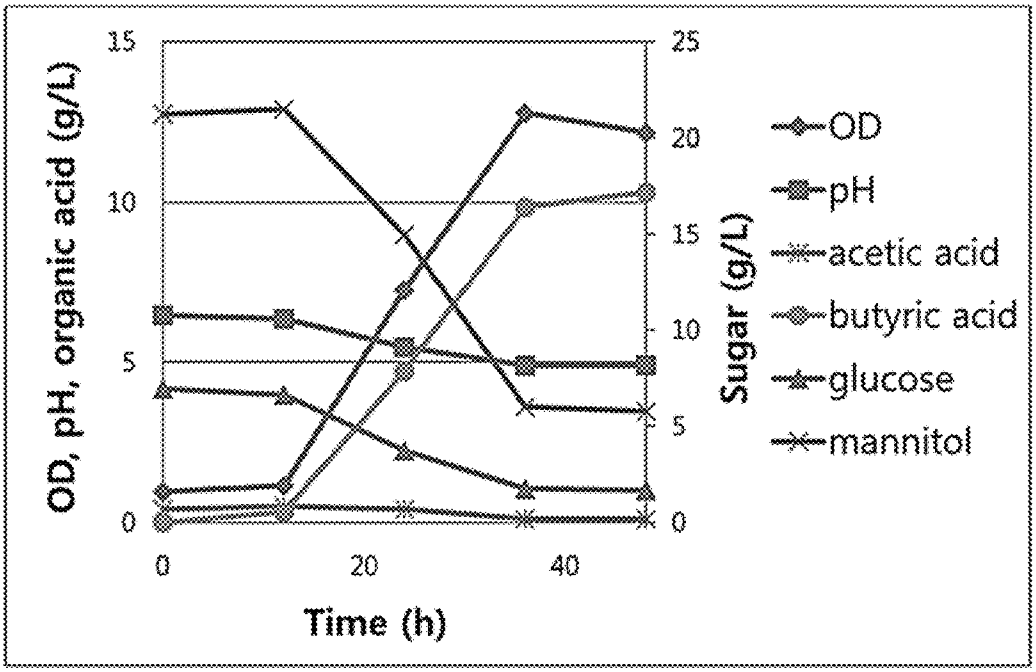
FIGS. 5*a*-5*c* show a result of analyzing the increase in fermentation efficiency of *Clostridium tyrobutyricum* ATCC 25755 for a mixture of seaweed biomass and lignocellulosic biomass depending on a weight ratio (FIG. 5*a*: seaweed: lignocellulosic=9:1, FIG. 5*b*: seaweed:lignocellulosic=8:2, FIG. 5*c*: seaweed:lignocellulosic=7:3).

FIG. 5*a* shows the growth of *Clostridium tyrobutyricum* ATCC 25755 for Example 1 (seaweed:lignocellulosic=9:1). After 48 hours of fermentation, 10.3 g/L of butyric acid was produced from 5.3 g/L of glucose and 15.5 g/L of mannitol. It can be seen that the consumption of the sugars and the production of the organic acid became very slow from 36 hours when acetic acid was depleted.

Figure 5B:
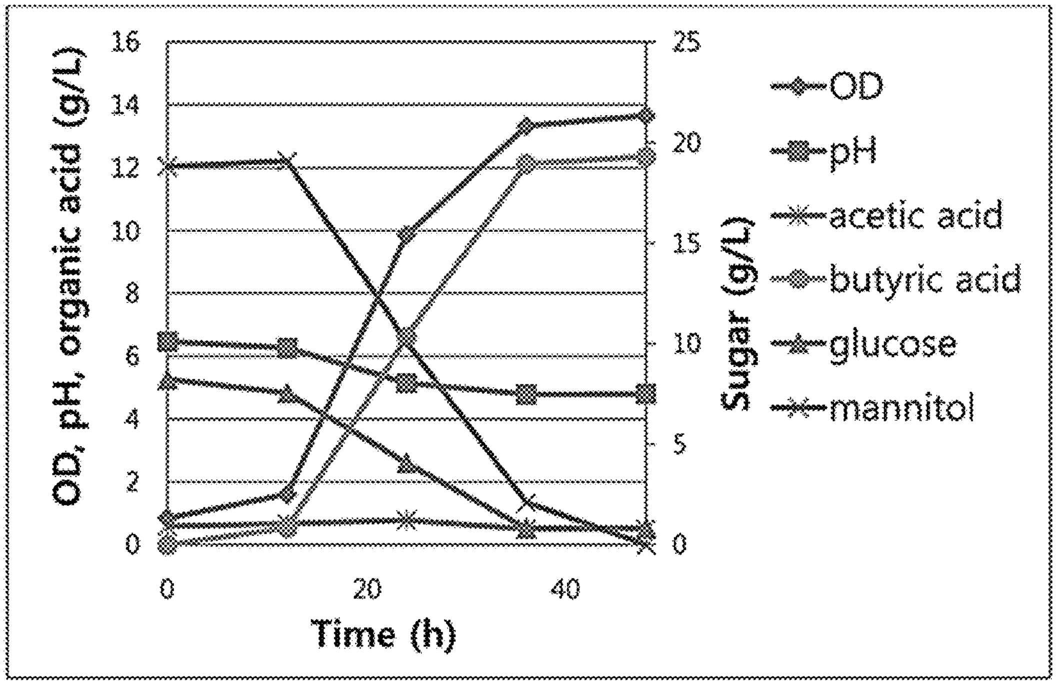

FIG. 5*b* shows the growth of *Clostridium tyrobutyricum* ATCC 25755 for Example 2 (seaweed:lignocellulosic=8:2). After 48 hours of fermentation, 12.4 g/L of butyric acid was produced from 7.4 g/L of glucose and 18.8 g/L of mannitol.

Figure 5C:
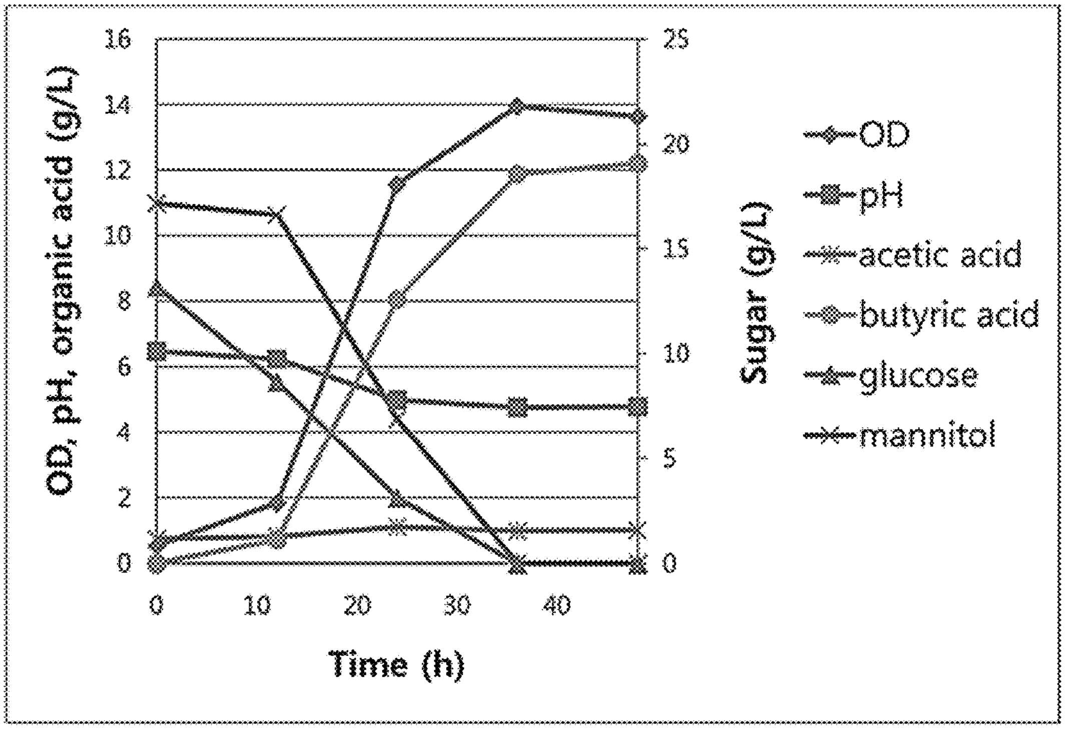

FIG. 5*c* shows the growth of *Clostridium tyrobutyricum* ATCC 25755 for Example 3 (seaweed:lignocellulosic=7:3). After 48 hours of fermentation, 12.2 g/L of butyric acid was produced from 13.2 g/L of glucose and 17.2 g/L of mannitol.

Figure 6:
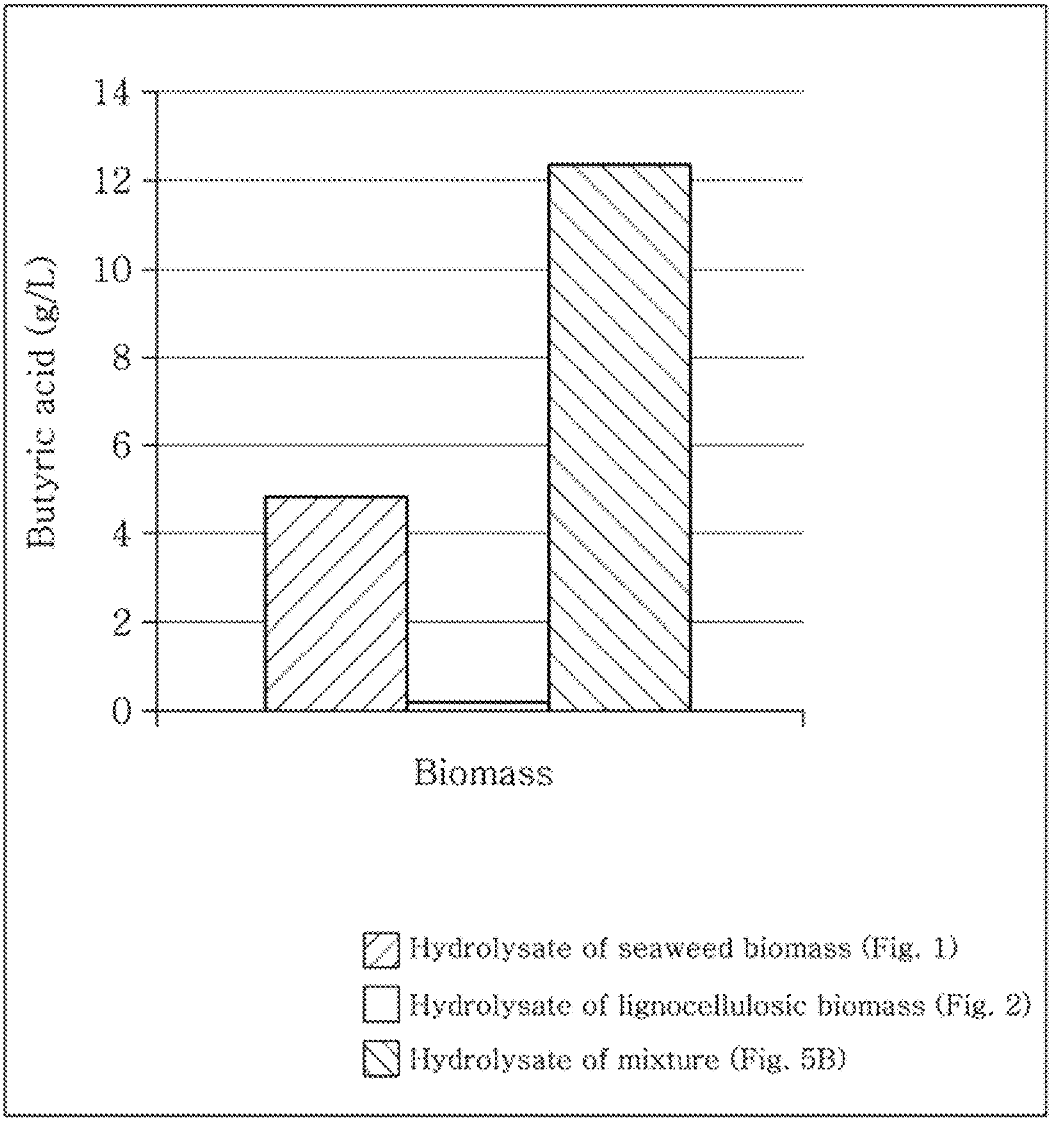
FIG. 6 shows a result of comparing the amount of butyric acid produced after 48 hours of fermentation as shown in FIG. 1 (seaweed biomass hydrolysate) and FIG. 2 (lignocellulosic biomass hydrolysate) with the amount of butyric acid produced after 48 hours of fermentation as shown in FIG. 5*b* (hydrolysate of a mixture of seaweed biomass and lignocellulosic biomass).

And, FIG. 6 compares the production of butyric acid after 48 hours of fermentation shown in FIG. 1 (Comparative Example 1) and FIG. 2 (Comparative Example 2) with the production of butyric acid after 48 hours of fermentation according to the present disclosure shown in FIG. 5*b* (Example 2).

tation efficiency by remarkably improving the growth of microorganisms and the production of organic acids.

[Test Example 4] Analysis of Fermentation Efficiency of Hydrolysate of Mixture of Seaweed Biomass and Lignocellulosic Biomass 2

In this example, a hydrolysate of a mixed biomass of seaweed biomass hydrolysate and lignocellulosic biomass hydrolysate was prepared as an exemplary embodiment of the present disclosure and the improvement in fermentation efficiency was analyzed.

First, 30% (w/v) of seaweed biomass (tangle) was pretreated at 121° C. for 30 minutes by adding to a 1.5% (w/v) sulfuric acid aqueous solution. A mannitol-containing hydrolysate was prepared without treatment with cellulase by adjusting pH to 6.5 using calcium hydroxide (Comparative Example 3). Also, a hydrolysate was prepared by pretreating 30% (w/v) of lignocellulosic biomass (waste wood) hydrolysate with 70% (w/v) sulfuric acid for 30 minutes and then hydrolyzing with 25% (w/v) sulfuric acid (Comparative Example 4). Then, pH was adjusted to 6.5 using calcium hydroxide.

Mixed biomass hydrolysates according to the present disclosure were prepared by mixing the prepared seaweed biomass (tangle) hydrolysate and lignocellulosic biomass (waste wood) hydrolysate. The seaweed biomass hydrolysate was diluted 4 times because the concentration of mannitol was too high for batch fermentation. The diluted seaweed biomass (tangle) hydrolysate and the lignocellulosic biomass (waste wood) hydrolysate were mixed at a volume ratio of 9:1 (Example 4) or 8.8:1.2 (Example 5).

The composition of the prepared hydrolysates is summarized in Table 2.

TABLE 2

| | Seaweed biomass, % (w/v) | Lignocellulosic biomass, % (w/v) | | Glucose | Xylose | Mannitol | Acetic acid | Total phenolics |
|---|---|---|---|---|---|---|---|---|
| Comp. Ex. 3 | 30 | 0 | Conc. (g/L) | 0 | 0 | 80 | 0 | N.D. |
| Comp. Ex. 4 | 0 | 30 | | 80 | 30 | 0 | 6 | 0.62 |
| Ex. 4 | 9 | 1 | | 7.12 | 0.75 | 15.46 | 0.32 | N.D. |
| Ex. 5 | 8.8 | 1.2 | | 8.24 | 0.9 | 19.83 | 0.49 | N.D. |

Acetic acid produced during the hydrolysis of lignocellulosic biomass has been considered as a fermentation inhibitor and various researches have been conducted to remove or reduce it [6, 7]. However, in accordance with the present disclosure, the lignocellulosic biomass-derived acetic acid which has been viewed as a fermentation inhibitor is consumed together during the fermentation of the seaweed biomass hydrolysate, thereby solving the redox potential imbalance problem. Accordingly, by using the hydrolysate of the mixed biomass of lignocellulosic biomass and seaweed biomass for the fermentation of butyric acid, remarkably improved fermentation efficiency can be achieved as compared to the hydrolysate of the lignocellulosic or seaweed biomass alone.

The present disclosure overcomes the disadvantage occurring when lignocellulosic biomass or seaweed biomass is used alone by using a mixture of the two types of biomass without an additional process. Accordingly, the present disclosure can provide a hydrolysate with superior fermen- Next, fermentation was conducted for each hydrolysate using *Clostridium tyrobutyricum* ATCC 25755 (American Type Culture Collection). For the fermentation, 5 g of yeast extract, 0.2 g of magnesium sulfate, 0.01 g of manganese sulfate, 0.01 g of iron sulfate, 0.01 g of sodium chloride, 0.5 g of monopotassium phosphate ($KH_2PO_4$), 0.5 g of dipotassium phosphate ($K_2HPO_4$) and 2 g of ammonium sulfate per liter were added to the hydrolysate. After adding 100 mM MES (2-(N-morpholino)ethanesulfonic acid) to prevent excessive decrease of pH due to the production of organic acids, initial pH was adjusted to 6.8 using 6 N potassium hydroxide (KOH). For batch culture, after adding 20 mL of a medium to a 60-mL serum bottle and then inoculating 2.5% of culture, culturing was conducted at 37° C. and 150 rpm in a shaking incubator.

The concentration of sugars and organic acids was measured for each culture. The concentration was analyzed by liquid chromatography (Agilent model 1200 liquid chromatograph). The sugars and butyric acid were analyzed using a refractive index detector and a Hi-Plex H column (300×7.8 mm, Agilent). The growth of microorganisms was analyzed by measuring absorbance at 600 nm using a spectrophotometer (UVmini-1240, Shimadzu).

Figure 7A:
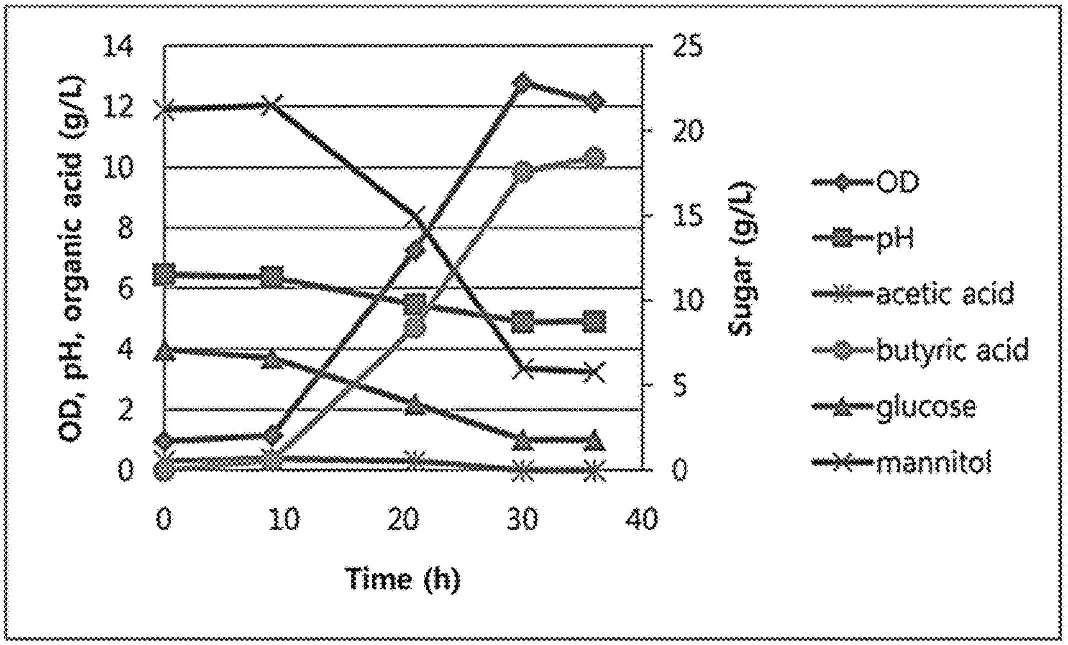
FIG. 7*a* and FIG. 7*b* show a result of analyzing the increase in fermentation efficiency of *Clostridium tyrobutyricum* ATCC 25755 for a mixture of seaweed biomass and lignocellulosic biomass depending on a weight ratio (FIG. 7*a*: seaweed biomass hydrolysate:lignocellulosic biomass hydrolysate=9:1, FIG. 7*b*: seaweed biomass hydrolysate: lignocellulosic biomass hydrolysate=8.8:1.2).

FIG. 7*a* shows the growth of *Clostridium tyrobutyricum* ATCC 25755 for Example 4 (seaweed:lignocellulosic=9:1). After 36 hours of fermentation, 10.3 g/L of butyric acid was produced from 5.3 g/L of glucose and 15.5 g/L of mannitol. It can be seen that the consumption of the sugars and the production of the organic acid became very slow from 36 hours when acetic acid was depleted.

Figure 7B:
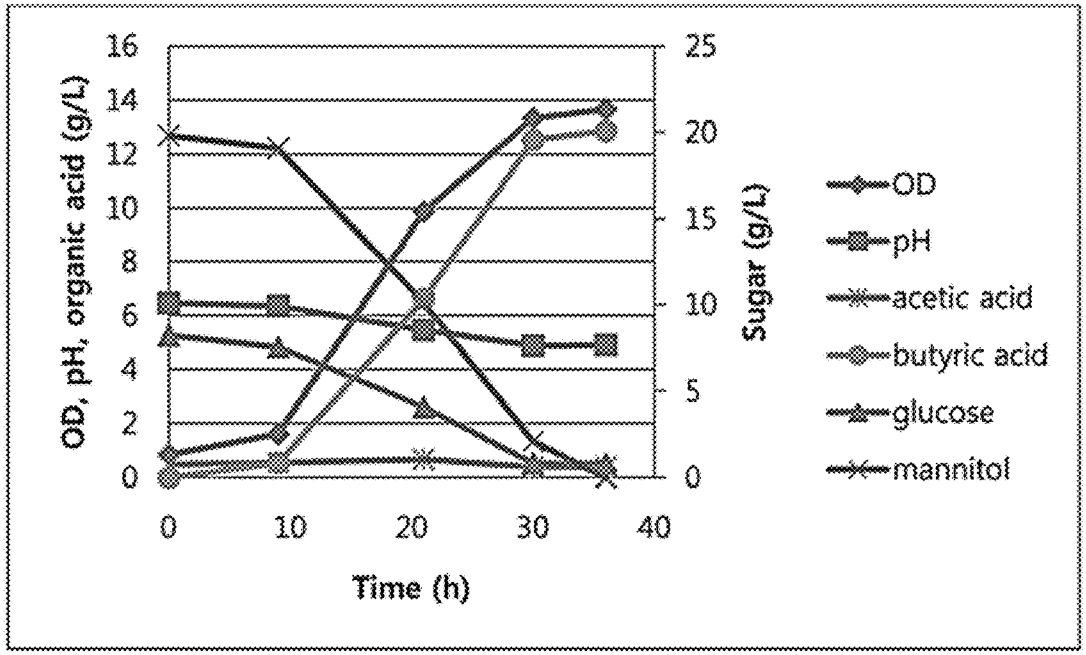

FIG. 7*b* shows the growth of *Clostridium tyrobutyricum* ATCC 25755 for Example 5 (seaweed:lignocellulosic=8.8:1.2). After 36 hours of fermentation, 12.9 g/L of butyric acid was produced from 7.4 g/L of glucose and 19.8 g/L of mannitol.

Accordingly, it can be seen that not only the mixed hydrolysate prepared by hydrolyzing a mixture of seaweed biomass and lignocellulosic biomass but also the mixed hydrolysate obtained by mixing a seaweed biomass hydrolysate and a lignocellulosic biomass hydrolysate exhibits remarkably improved fermentation efficiency as compared to a hydrolysate of seaweed biomass or lignocellulosic biomass only.

Through this, it can be seen that, when different types of biomass with different pretreatment and hydrolysis conditions are used, high hydrolysis yield can be maintained by optimizing the hydrolysis condition for each biomass. Also, by mixing the hydrolysates prepared under optimized hydrolysis conditions, the hydrolysis yield and fermentation efficiency of biomass can be improved at the same time.

What is claimed is:

1. A hydrolysate for use in fermentation by microorganisms, the hydrolysate being a hydrolysate of a mixture of seaweed biomass and lignocellulosic biomass, wherein the hydrolysate is configured to generate lignocellulosic biomass-derived acetic acid and seaweed biomass-derived mannitol when fermented together, and the generated acetic acid and mannitol are consumed when the hydrolysate is fermented, wherein the seaweed biomass is one or more selected from red algae, brown algae, and green algae.

2. The hydrolysate according to claim 1, wherein the seaweed biomass is brown algae biomass.

3. The hydrolysate according to claim 1, wherein the hydrolysate comprises fermentation inhibitors naturally present without external removal of fermentation inhibitors in an amount of at least 50 wt % less than an amount of fermentation inhibitors naturally present without external removal of fermentation inhibitors in a lignocellulosic biomass hydrolysate based on the total volume of the hydrolysate, when the amount of the mixture of seaweed biomass and lignocellulosic biomass is the same as the lignocellulosic biomass of the lignocellulosic biomass hydrolysate, and the fermentation inhibitors comprise one or more of phenolic compounds and furan-based compounds.

4. The hydrolysate according to claim 1, wherein the mixture of seaweed biomass and lignocellulosic biomass has a weight ratio of seaweed biomass and lignocellulosic biomass of 9:1-1:9.

5. The hydrolysate according to claim 1, wherein the hydrolysate is configured to generate fermentation inhibitors in an amount of at least 80 wt % less than an amount of fermentation inhibitors generated by a lignocellulosic biomass hydrolysate based on the total volume of the hydrolysate, when the amount of the mixture of seaweed biomass and lignocellulosic biomass is the same as the lignocellulosic biomass of the lignocellulosic biomass hydrolysate.

6. The hydrolysate according to claim 3, wherein the fermentation inhibitor comprises one or more selected from:

one or more phenolic compound selected from a group consisting of ferulic acid, coumaric acid, benzoic acid, syringic acid, vanillic acid, vanillin, 4-hydroxybenzoic acid, 4-hydroxybenzaldehyde and syringaldehyde; and one or more furan-based compound selected from a group consisting of furan, furfural and 5-hydroxymethylfurfural (5-HMF).

7. The hydrolysate according to claim 1, wherein the hydrolysate of a mixture of seaweed biomass and lignocellulosic biomass comprises 75-100 wt % of sugar as compared to a lignocellulosic biomass hydrolysate based on the total volume of the hydrolysate when the amount of the mixture of seaweed biomass and lignocellulosic biomass is the same as the lignocellulosic biomass of the lignocellulosic biomass hydrolysate.

8. The hydrolysate according to claim 7, wherein the sugar is one or more selected from a group consisting of a monosaccharide; a disaccharide; and one or more and a polysaccharide, wherein the monosaccharide is one or more selected from a group consisting of glucose, galactose, mannose, rhamnose, xylose and arabinose, wherein the disaccharide is cellobiose, and wherein the polysaccharide is one or more selected from a group consisting of mannitol, alginic acid and laminaran.

9. A hydrolysate for use in fermentation by microorganisms, the hydrolysate being a mixture of a hydrolysate of seaweed biomass and a hydrolysate of lignocellulosic biomass, wherein the hydrolysate mixture comprises lignocellulosic biomass-derived acetic acid and seaweed biomass-derived mannitol, wherein the hydrolysate mixture comprises the acetic acid in a proportion to be consumed together with the mannitol when the hydrolysate mixture is fermented, wherein the seaweed biomass is one or more selected from red algae, brown algae, and green algae.

10. The hydrolysate according to claim 9, wherein the seaweed biomass is brown algae biomass.

11. The hydrolysate according to claim 9, wherein the mixture of a hydrolysate of seaweed biomass and a hydrolysate of lignocellulosic biomass is configured to generate fermentation inhibitors in an amount of at least 50 wt % less than an amount of fermentation inhibitors generated by a lignocellulosic biomass hydrolysate based on the total volume of the hydrolysate, when the amount of the mixture of seaweed biomass and lignocellulosic biomass is the same as the lignocellulosic biomass of the lignocellulosic biomass hydrolysate, and the fermentation inhibitors comprise one or more of phenolic compounds and furan-based compounds.

12. The hydrolysate according to claim 9, wherein the mixture of a hydrolysate of seaweed biomass and a hydrolysate of lignocellulosic biomass has a weight ratio of seaweed biomass and lignocellulosic biomass of 9:1-1:9.

13. The hydrolysate according to claim 9, wherein the mixture of a hydrolysate of seaweed biomass and a hydrolysate of lignocellulosic biomass comprises fermentation inhibitors naturally present without external removal of fermentation inhibitors in an amount of at least 80 wt % less than an amount of fermentation inhibitors naturally present without external removal of fermentation inhibitors in a lignocellulosic biomass hydrolysate based on the total volume of the hydrolysate, when the amount of the mixture of seaweed biomass and lignocellulosic biomass is the same as the lignocellulosic biomass of the lignocellulosic biomass hydrolysate.

14. The hydrolysate according to claim 11, wherein the fermentation inhibitor comprises one or more selected from:

one or more phenolic compound selected from a group consisting of ferulic acid, coumaric acid, benzoic acid, syringic acid, vanillic acid, vanillin, 4-hydroxybenzoic acid, 4-hydroxybenzaldehyde and syringaldehyde; and one or more furan-based compound selected from a group consisting of furan, furfural and 5-hydroxymethylfurfural (5-HMF).

15. The hydrolysate according to claim 9, wherein the mixture of a hydrolysate of seaweed biomass and a hydrolysate of lignocellulosic biomass comprises 75-100 wt % of a sugar as compared to a lignocellulosic biomass hydrolysate when the amount of the mixture of seaweed biomass and lignocellulosic biomass is the same as the lignocellulosic biomass of the lignocellulosic biomass hydrolysate.

16. The hydrolysate according to claim 15, wherein the sugar is one or more selected from a monosaccharide; a disaccharide; and a polysaccharide, wherein the monosaccharide is one or more selected from a group consisting of glucose, galactose, mannose, rhamnose, xylose, and arabinose, wherein the disaccharide is cellobiose, and wherein the polysaccharide is one or more selected from a group consisting of mannitol, alginic acid and laminaran.

* * * * *